US006107025A

United States Patent [19]
Caskey et al.

[11] Patent Number: 6,107,025
[45] Date of Patent: *Aug. 22, 2000

[54] DIAGNOSIS OF THE FRAGILE X SYNDROME

[75] Inventors: C. Thomas Caskey; David L. Nelson; Maura Pieretti, all of Houston, Tex.; Stephen T. Warren, Clarkston, Ga.; Ben A. Oostra, Rotterdam, Netherlands

[73] Assignee: Baylor College of Medicine, Houston, Tex.

[ * ] Notice: This patent is subject to a terminal disclaimer.

[21] Appl. No.: 07/705,490

[22] Filed: May 24, 1991

[51] Int. Cl.[7] .......................... C07H 21/02; C07H 21/04; C12Q 1/68; C12P 19/34

[52] U.S. Cl. ........................ 435/6; 435/91.2; 536/23.1; 536/24.33; 536/24.1

[58] Field of Search ..................... 435/91.2, 6; 536/27, 536/23.1, 24.1, 24.33; 935/77, 78

[56] References Cited

PUBLICATIONS

M. Pieretti, et al., "Absence of Expression of the FMR–1 Gene in Fragile X Syndrome" *Cell* 66:817–822 (1991).

J.S. Sutcliffe, et al., "DNA methylation represses FMR–1 transcription in fragile X syndrome" *Human Molecular Genetics* 1:397–400 (1992).

D. Devys, et al., "The FMR–1 protein is cytoplasmic, most abundant in neurons and appears normal in carriers of a fragile X premutation" *Nature Genetics* 4:335–340 (1993).

H. Siomi, et al., "The Protein Product of the Fragile X Gene, FMR1, Has Characteristics of an RNA–Binding Protein" *Cell* 74:291–298 (1993).

C. Verheij, et al., "Characterization and localization of the FMR–1 gene product associated with fragile X syndrome" *Nature* 363:722–724 (1993).

D.P.A. Kuhl, et al., "Fragile X Syndrome Protein FMRP Associates with the Microfilament Fraction of the Cellular Cytoskeleton" Submission to *Cell*.

Heitz etal. Science vol. 251 pp 1236–1239. Mar. 8, 1991.

Suthers, et al., "Physical mapping of new DNA probes near the Fragile X mutation (FRAXA) by using a panel of cell lines" *American Journal of Human Genetics* 47:187–195 (1990). This paper provides order for a number of cloned DNAs using a panel of somatic cell hybrid breakpoints near the Fragile X site. The order of the breakpoints is likewise established by the probes.

Warren, et al., "Isolation of the human chromosomal band Xq28 within somatic cell hybrids by Fragile X site breakage" *Proceedings of the National Academy of Sciences* 87:3856–3860 (1990). This paper describes a panel of hybrid cell lines with chromosome breakpoints at or near the Fragile X site, and its use as a mapping reagent.

Warren, et al., "The Fragile X site in somatic cell hybrids; An approach for molecular cloning of Fragile sites" *Science* 237:420–423 (1987). This paper describes the first hybrid cell lines with chromosome breakpoints at or near the Fragile X site, and the potential for using these to identify the site.

Warren, et al., "Strategy for molecular cloning of the Fragile X site DNA" *American Journal of Medical Genetics* 30:613–623 (1988). This paper describes the strategy of using somatic cell hybrids with Fragile X breakpoints for identifying the Fragile X site.

Warren and Davidson, "Expression of Fragile X chromosome in human–rodent somatic cell hybrids" *Somatic Cell and Molecular Genetics* 10:409–413 (1984). This paper demonstrates that the Fragile X site is expressed in rodent cell backgrounds.

Warren, "Molecular and somatic cell genetic approaches to the Fragile X syndrome" in: Brosius, J and Fremeau, RT (eds.) *Molecular Genetic Approaches to Neuropsychiatric Disease* (Academic Press, San Diego) 1991. A review of state of art.

Brown, "Invited editorial: The Fragile X" Progress toward solving the puzzle *American Journal of Human Genetics* 47:175–180 (1990). A review of the status of the physical map as of one year prior to the Fragile X site identification.

Nussbaum and Ledbetter, "The Fragile X syndrome" Chapter 8 of *The Metabolic Basis of Inherited Disease*, 6th edition, McGraw–Hill, 1989. A comprehensive review of Fragile X syndrome.

Nussbaum and Ledbetter, "Fragile X syndrome: A unique mutation in man" *Annual Reveiw of Genetics* 20:109–145 (1986). Review of the genetic aspects of Fragile X syndrome.

Heitz, et al., "Isolation of sequences that span the Fragile X and identification of a Fragile X–related CpG island" *Science* 251:1236–1239 (1991). This paper describes localization of the Fragile X site on a large fragment of DNA and the positions of somatic cell hybrid chromosome breakpoints within the region. It also localizes a CpG island showing Fragile X specific methylation patterns.

Craig, "Methylation and the Fragile X" *Nature* 349:742–743 (1991). This news article reviews papers L & M where Fragile X specific methylation was reported.

Bell, et al., "Physical mapping across the Fragile X" Hypermethylation and clinical expression of the Fragile X syndrome *Cell* 64:851–866 (1991). This paper describes long–range restriction mapping experiments that determined Fragile X specific hypermethylation of a CpG island in numerous patients.

Vincent, et al., "Abnormal pattern detected in Fragile–X patients by pulsed–field gel electrophoresis" *Nature* 349:624–626 (1991). This paper describes long–range restriction mapping experiments that determined Fragile X specific hypermethylation of a CpG island in numerous patients.

*Primary Examiner*—Stephanie Zitomer
*Attorney, Agent, or Firm*—Fulbright & Jaworski LLP

[57] ABSTRACT

A sequence of the FMR-1 gene is disclosed. This sequence and related probes, cosmids and unique repeats are used to detect X-linked diseases and especially the fragile X syndrome.

4 Claims, 10 Drawing Sheets

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 3765 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
GACGGAGGCG CCCGTGCCAG GGGGCGTGCG GCAGCGCGGC GGCGGCGGCG GCGGCGGCGG      60

CGGCGGAGGC GGCGGCGGCG GCGGCGGCGG CGGCGGAGGC GGCGGCGGCG GCGGCGGCGG     120

CGGCGGCTGG GCCTCGAGCG CCCGCAGCCC ACCTCTCGGG GGCGGGCTCC CGGCGCTAGC     180

AGGGCTGAAG AGAAGATGGA GGAGCTGGTG GTGGAAGTGC GGGGCTCCAA TGGCGCTTTC     240

TACAAGGCAT TTGTAAAGGA TGTTCATGAA GATTCAATAA CAGTTGCATT TGAAAACAAC     300

TGGCAGCCTG ATAGGCAGAT TCCATTTCAT GATGTCAGAT TCCCACCTCC TGTAGGTTAT     360

AATAAAGATA TAAATGAAAG TGATGAAGTT GAGGTGTATT CCAGAGCAAA TGAAAAAGAG     420

CCTTGCTGTT GGTGGTTAGC TAAAGTGAGG ATGATAAAGG GTGAGTTTTA TGTGATAGAA     480

TATGCAGCAT GTGATGCAAC TTACAATGAA ATTGTCACAA TTGAACGTCT AAGATCTGTT     540

AATCCCAACA AACCTGCCAC AAAAGATACT TTCCATAAGA TCAAGCTGGA TGTGCCAGAA     600

GACTTACGGC AAATGTGTGC CAAAGAGGCG GCACATAAGG ATTTTAAAAA GGCAGTTGGT     660

GCCTTTTCTG TAACTTATGA TCCAGAAAAT TATCAGCTTG TCATTTTGTC CATCAATGAA     720

GTCACCTCAA AGCGAGCACA TATGCTGATT GACATGCACT TCGGAGTCT GCGCACTAAG      780

TTGTCTCTGA TAATGAGAAA TGAAGAAGCT AGTAAGCAGC TGGAGAGTTC AAGGCAGCTT     840

GCCTCGAGAT TTCATGAACA GTTTATCGTA AGAGAAGATC TGATGGGTCT AGCTATTGGT     900

ACTCATGGTG CTAATATTCA GCAAGCTAGA AAAGTACCTG GGTCACTGC TATTGATCTA       960

GATGAAGATA CCTGCACATT TCATATTTAT GGAGAGGATC AGGATGCAGT GAAAAAAGCT    1020

AGAAGCTTTC TCGAATTTGC TGAAGATGTA ATACAAGTTC CAAGGAACTT AGTAGTAATA    1080

GGAAAAAATG GAAAGCTGAT TCAGGAGATT GTGGACAAGT CAGGAGTTGT GAGGGTGAGG    1140

ATTGAGGCTG AAAATGAGAA AAATGTTCCA CAAGAAGAGG AAATTATGCC ACCAAATTCC    1200

CTTCCTTCCA ATAATTCAAG GGTTGGACCT AATGCCCCAG AAGAAAAAAA ACATTTAGAT    1260

ATAAAGGAAA ACAGCACCCA TTTTTCTCAA CCTAACAGTA CAAAAGTCCA GAGGGGTATG    1320

GTACCATTTG TTTTTGTGGG AACAAAGGAC AGCATCGCTA ATGCCACTGT TCTTTTGGAT    1380

TATCACCTGA ACTATTTAAA GGAAGTAGAC CAGTTGCGTT TGGAGAGATT ACAAATTGAT    1440

GAGCAGTTGC GACAGATTGG AGCTAGTTCT AGACCACCAC CAAATCGTAC AGATAAGGAA    1500

AAAAGCTATG TGACTGATGA TGGTCAAGGA ATGGGTCGAG GTAGTAGACC TTACAGAAAT    1560

AGGGGGCACG GCAGACGCGG TCCTGGATAT ACTTCAGGAA CTAATTCTGA AGCATCAAAT    1620

GCTTCTGAAA CAGAATCTGA CCACAGAGAC GAACTCAGTG ATTGGTCATT AGCTCCAACA    1680

GAGGAAGAGA GGGAGAGCTT CCTGCGCAGA GGAGACGGAC GGCGGCGTGG AGGGGGAGGA    1740

AGAGGACAAG GAGGAAGAGG ACGTGGAGGA GGCTTCAAAG GAAACGACGA TCACTCCCGA    1800

ACAGATAATC GTCCACGTAA TCCAAGAGAG GCTAAAGGAA GAACAACAGA TGGATCCCTT    1860

CAGAATACCT CCAGTGAAGG TAGTCGGCTG CGCACGGGTA AGATCGTAA CCAGAAGAAA      1920

GAGAAGCCAG ACAGCGTGGA TGGTCAGCAA CCACTCGTGA ATGGAGTACC CTAAACTGCA    1980

TAATTCTGAA GTTATATTTC CTATACCATT TCCGTAATTC TTATTCCATA TTAGAAAACT    2040

TTGTTAGGCC AAAGACAAAT AGTAGGCAAG ATGGCACAGG GCATGAAATG AACACAAATT    2100

ATGCTAAGAA TTTTTTATTT TTTGGTATTG GCCATAAGCA ACAATTTTCA GATTTGCACA    2160
```

-continued

```
AAAAGATACC TTAAAATTTG AAACATTGCT TTTAAAACTA CTTAGCACTT CAGGGCAGAT    2220

TTTAGTTTTA TTTTCTAAAG TACTGAGCAG TGATATTCTT TGTTAATTTG GACCATTTTC    2280

CTGCATTGGG TGATCATTCA CCAGTACATT CTCAGTTTTT CTTAATATAT AGCATTTATG    2340

GTAATCATAT TAGACTTCTG TTTTCAATCT CGTATAGAAG TCTTCATGAA ATGCTATGTC    2400

ATTTCATGTC CTGTGTCAGT TTATGTTTTG GTCCACTTTT CCAGTATTTT AGTGGACCCT    2460

GAAATGTGTG TGATGTGACA TTTGTCATTT TCATTAGCAA AAAAAGTTGT ATGATCTGTG    2520

CCTTTTTTAT ATCTTGGCAG GTAGGAATAT TATATTTGGA TGCAGAGTTC AGGGAAGATA    2580

AGTTGGAAAC ACTAAATGTT AAAGATGTAG CAAACCCTGT CAAACATTAG TACTTTATAG    2640

AAGAATGCAT GCTTTCCATA TTTTTTTCCT TACATAAACA TCAGGTTAGG CAGTATAAAG    2700

AATAGGACTT GTTTTTGTTT TTGTTTTGTT GCACTGAAGT TTGATAAATA GTGTTATTGA    2760

GAGAGATGTG TAATTTTTCT GTATAGACAG GAGAAGAAAG AACTATCTTC ATCTGAGAGA    2820

GGCTAAAATG TTTTCAGCTA GGAACAAATC TTCCTGGTCG AAAGTTAGTA GGATATGCCT    2880

GCTCTTTGGC CTGATGACCA ATTTTAACTT AGAGCTTTTT TTTTTAATTT TGTCTGCCCC    2940

AAGTTTTGTG AAATTTTTCA TATTTTAATT TCAAGCTTAT TTTGGAGAGA TAGGAAGGTC    3000

ATTTCCATGT ATGCATAATA ATCCTGCAAA GTACAGGTAC TTTGTCTAAG AAACATTGGA    3060

AGCAGGTTAA ATGTTTTGTA AACTTTGAAA TATATGGTCT AATGTTTAAG CAGAATTGGA    3120

AAAGACTAAG ATCGGTTAAC AAATAACAAC TTTTTTTTCT TTTTTTCTTT TGTTTTTTGA    3180

AGTGTTGGGG TTTGGTTTTG TTTTTTGAGT CTTTTTTTTT TAAGTGAAAT TTATTGAGGA    3240

AAAATATGTG AAGGACCTTC ACTCTAAGAT GTTATATTTT TCTTAAAAAG TAACTCCTAG    3300

TAGGGGTACC ACTGAATCTG TACAGAGCCG TAAAAACTGA AGTTCTGCCT CTGATGTATT    3360

TTGTGAGTTT GTTTCTTTGA ATTTTCATTT TACAGTTACT TTTCCTTGCA TACAAACAAG    3420

CATATAAAAT GGCAACAAAC TGCACATGAT TTCACAAATA TTAAAAAGTC TTTTAAAAAG    3480

TATTGCCAAA CATTAATGTT GATTTCTAGT TATTTATTCT GGGAATGTAT AGTATTTGAA    3540

AACAGAAATT GGTACCTTGC ACACATCATC TGTAAGCTGT TTGGTTTTAA AATACTGTAG    3600

ATAATTAACC AAGGTAGAAT GACCTTGTAA TGTAACTGCT CTTGGGCAAT ATTCTCTGTA    3660

CATATTAGCG ACAACAGATT GGATTTTATG TTGACATTTG TTTGGTTATA GTGCAATATA    3720

TTTTGTATGC AAGCAGTTTC AATAAAGTTT GATCTTCCTC TGCTA              3765
```

(2) INFORMATION FOR SEQ ID NO:2:

(i) SEQUENCE CHARACTERISTICS:
        (A) LENGTH: 4242 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:2:

```
ACTTGGAGGG GTATAATCAT TCTAATCAAT GTGTCCCCTT TTACTATAAT ACATTGGAGT      60

TGCAGCTAAT GCTCTGCTCC CATTCAGCCT ATGATGAGAT TCTCTTTCAG CCCTATTGGG     120

TTCTTGGCCT CATGTGACTA CTCCAAAGAC CCTAGTCCAA AAGGTCTTTC CTGTTTGCTA     180

TGGCCTTGAG GAATGTGGCC CTAGATCCAC CGCTTTAAAG CTGGAGTTCC ACCAGCAGCA     240

ACATCCTCTC ATTCTGGGGC ACCTGCCTGG GGCAGGTCAT CCTGCCTCTG CCAACTCAGT     300
```

```
GCTATTAGTT AACTCTCACC TGCCATATTC CAGCTGGAAT CATCTCCCCT TCTCCACCCC    360

AGACTAGGTC ATGTTCCGCC ATCATGGAAG CGCCTATTCT TCATACCCCT TATCACAGCT    420

GCAACTACTC ATTTACTTGT CTGACAATTT GATTTATGTC CACCTACTTT GCTAGGTACT    480

AAGTTCAATG CTGGCAGTCG TTTCTTCTTT TTTTTTCTTT TCTGTTTTGC TCACCGATTT    540

CTCGTTAGCA CTTAGCACAG TGTCTGGCAC ACGATAGATG CTCCGTCAAC TTCTCAGTTG    600

GATACCAGCA TCCCGAAGGG ACATGGATTA AGGCAGCTAT AAGCACGGTG TAAAAACAGG    660

AATAAGAAAA AGTTGAGGTT TGTTTCACAG TGGAATGTAA AGGGTTGCAA GGAGGTGCAT    720

CGGCCCCTGT GGACAGGACG CATGACTGCT ACACACGTGT TCACCCCACC CTCTGGCACA    780

GGGTGCACAT ACAGTAGGGG CAGAAATGAA CCTCAAGTGC TTAACACAAT TTTTAAAAAA    840

TATATAGTCA AGTGAAAGTA TGAAAATGAG TTGAGGAAAG GCGAGTACGT GGGTCAAAGC    900

TGGGTCTGAG GAAAGGCTCA CATTTTGAGA TCCCGACTCA ATCCATGTCC CTTAAAGGGC    960

ACAGGGTGTC TCCACAGGGC CGCCCAAAAT CTGGTGAGAG AGGGCGTAGA CGCCTCACCT   1020

TCTGCCTCTA CGGGTCACAA AAGCCTGGGT CACCCTGGTT GCCACTGTTC CTAGTTCAAA   1080

GTCTTCTTCT GTCTAATCCT TCACCCCTAT TCTCGCCTTC CACTCCACCT CCCGCTCAGT   1140

CAGACTGCGC TACTTTGAAC CGGACCAAAC CAAACCAAAC CAAACCAAAC CAAACCAGAC   1200

CAGACACCCC CTCCCGCGGA ATCCCAGAGA GGCCGAACTG GGATAACCGG ATGCATTTGA   1260

TTTCCCACGC CACTGAGTGC ACCTCTGCAG AAATGGGCGT TCTGGCCCTC GCGAGGCAGT   1320

GCGACCTGTC ACCGCCCTTC AGCCTTCCCG CCCTCCACCA AGCCCGCGCA CGCCCGGCCC   1380

GCGCGTCTGT CTTTCGACCC GGCACCCCGG CCGGTTCCCA GCAGCGCGCA TGCGCGCGCT   1440

CCCAGGCCAC TTGAAGAGAG AGGGCGGGGC CGAGGGGCTG AGCCCGCGGG GGGAGGGAAC   1500

AGCGTTGATC ACGTGACGTG GTTTCAGTGT TTACACCCGC AGCGGGCCGG GGGTTCGGCC   1560

TCAGTCAGGC GCTCAGCTCC GTTTCGGTTT CACTTCCGGT GGAGGGCCGC CTCTAGCGGG   1620

CGGCGGGCCG ACGGCGAGCG CGGGCGGCGG CGGTGACGGA GGCGCCGCTG CCAGGGGGCG   1680

TGCGGCAGCG CGGCGGCGGC GGCGGCGGCG GCGGCGGCGG CGGCGGCGGC GGCGGCGGCT   1740

GGGCCTCGAG CGCCCGCAGC CCACCTCTTG GGGGCGGGCT CCCGGCGCTA CAGGGCTGAA   1800

GAGAAGATGG AGGAGCTGGT GGTGGAAGTG CGGGCTCCAA TGGCGCTTTC TACAAGGTAC   1860

TTGGCTCTAG GGCAGGCCCC ATCTTCGCCC TTCCTTCCCT CCCTTTTTTC TTGGTGTCGG   1920

CGGGAGGCAG GCCCGGGGCC CTCTTCCCGA GCACCGCGCC TGGGTGCCAG GGCACGCTCG   1980

GCGGGATGTT GTTGGGAGGG AAGGACTGGA CTTGGGGCCT GTTGGAAGCC CCTCTCCGAC   2040

TCCAGAGGCC CTAGCGCCTA TCGAAATGAG AGACCAGCGA GGAGAGGGTT CTCTTTCGGC   2100

GCCGAGCCCC GCCGGGGTGA GCTGGGGATG GGCGAGGGCC GGCGGCAGGT ACTAGAGCCG   2160

GGCGGGAAGG GCCGAAATCG GCGCTAAGTG ACGGCGATGG CTTATTCCCC CTTTCCTAAA   2220

CATCATCTCC CAGCGGGATC CGGGCCTGTC GTGTGGGTAG TTGTGGAGGA GCGGGGGGCG   2280

CTTCAGCCGG GCCGCCTCCT GCAGCGCCAA GAGGGCTTCA GGTCTCCTTT GGCTTCTCTT   2340

TTCCGGTCTA GCATTGGGAC TTCGGAGAGC TCCACTGTTC TGGGCGAGGG CTGTGAAGAA   2400

AGAGTAGTAA GAAGCGGTAG TCGGCACCAA ATCACAATGG CAACTGATTT TTAGTGGCTT   2460

CTCTTTGTGG ATTTCGGAGG AGATTTTAGA TCCAAAAGTT TCAGGAAGAC CCTAACATGG   2520

CCCAGCAGTG CATTGAAGAA GTTGATCATC GTGAATATTC GCGTCCCCCT TTTTGTTAAA   2580

CGGGGTAAAT TCAGGAATGC ACATGCTTCA GCGTCTAAAA CCATTAGCAG CGCTGCTACT   2640
```

-continued

```
TAAAAATTGT GTGTGTGTGT TTAAGTTTCC AAAGACCTAA ATATATGCCA TGAAACTTCA      2700

GGTAATTAAC TGAGAGTATA TTATTACTAG GGCATTTTTT TTTTAACTGA GCGAAAATAT      2760

TTTTGTGCCC CTAAGAACTT GACCACATTT CCTTTGAATT TGTGGTGTTG CAGTGGACTG      2820

AATTGTTGAG GCTTTATATA GGCATTCATG GGTTTACTGT GCTTTTTAAA GTTACACCAT      2880

TGCAGATCAA CTAACACCTT TCAGTTTTAA AAGGAAGATT TACAAATTTG ATGTAGCAGT      2940

AGTGCGTTTG TTGGTATGTA GGTGCTGTAT AAATTCATCT ATAAATTCTC ATTTCCTTTT      3000

GAATGTCTAT AACCTCTTTC AATAATATCC CACCTTACTA CAGTATTTTG GCAATAGAAG      3060

GTGCGTGTGG AAGGAAGGCT GGAAAATAGC TATTAGCAGT GTCCAACACA ATTCTTAAAT      3120

GTATTGTAGA ATGGCTTGAA TGTTTCAGAC AGGACACGTT TGGCTATAGG AAAATAAACA      3180

ATTGACTTTA TTCTGTGTTT ACCAATTTTA TGAAGACATT TGGAGATCAG TATATTTCAT      3240

AAATGAGTAA AGTATGTAAA CTGTTCCATA CTTTGAGCAC AAAGATAAAG CCTTTTGCTG      3300

TAAAAGGAGG CAAAAGGTAA CCCCGCGTTT ATGTTCTTAA CAGTCTCATG AATATGAAAT      3360

TGTTTCAGTT GACTCTGCAG TCAAAATTTT AATTTCATTG ATTTTATTGA TCCATAATTT      3420

CTTCTGGTGA GTTTGCGTAG AATCGTTCAC GGTCCTAGAT TAGTGGTTTT GGTCACTAGA      3480

TTTCTGGCAC TAATAACTAT AATACATATA CATATATATG TGTGAGTAAC GGCTAATGGT      3540

TAGGCAAGAT TTTGATTGAC CTGTGATATA AACTTAGATT GGATGCCACT AAAGTTTGCT      3600

TATCACAGAG GGCAAGTAGC ACATTATGGC CTTGAAGTAC TTATTGTTCT CTTCCAGCAA      3660

CTTATGATTT GCTCCAGTGA TTTTCTTGCA CACTGACTGG AATATAAGAA ATGCCTTCTA      3720

TTTTTGCTAT TAATTCCCTC CTTTTTTGTT TTGTTTTGTA ACGAAGTTGT TAACTTGAA       3780

GGTGAATGAA GAATAGGTTG GTTGCCCCTT AGTTCCCTGA GGAGAAATGT TAATACTTGA      3840

ACAAGTGTGT GTCAGACAAA TTGCTGTTAT GTTTATTTAA TTAAGTTTGA TTTCTAAGAA      3900

AATCTCAAAT GGTCTGCACT GATGGAAGAA CAGTTTCTGT AACAAAAAAG CTTGAAATTT      3960

TTATATGACT TATAATACTG CTGTGAGTTT TAAAAGTAAA GCAAAAGTAA ACTGAGTTGC      4020

TTGTCCAGTG GGATGGACAG GAAAGATGTG AAATAAAAAC CAATGAAAAA TGAACTGCTG      4080

TGGAGAAGTG TTACATTTAT GGAAAAAGAA ATAGGAACCT TGTTCATCAA ATTGATAGAA      4140

AAGCTTTTAA AACTAAACAA ATCAAACAAC TTGAGTATAA TGGAATTCAG GTAAGCTATC      4200

TTGAAAGGGG AAATATCAAA AGCTAGAGAT CAGAGTAAGG CT                         4242
```

(2) INFORMATION FOR SEQ ID NO:3:

(i) SEQUENCE CHARACTERISTICS:
        (A) LENGTH: 229 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:3:

```
GAATTCAGGT AAGCTATCTT GAAAGGGGAA ATATCAAAAG CTAGAGATCA GAGTAAGGCT       60

GAGACTCAGA GTCAAGTGGG GAAGACTAAG TTGCAGTATG TACTGGCAGT GAAGATAAGT      120

ATTTATTCAT TCATTGAACA TACCTTGAAA TCAACCACTT TTAATGTGCC AGGGACACAA      180

AGATAGAAAA GACATTTGCC CTGTCTGGAA GGTACTAATA ATCCAATAA                  229
```

```
(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:4:

CTTGCCAACC GTTCAGCCAC                                                   20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:5:

ATTTCCTGGA GCACAGACTG                                                   20

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:6:

AGAGCTTCAC TATGCAATGG AATC                                              24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:7:

GTACATTAGA GTCACCTGTG GTGC                                              24

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(xi) SEQUENCE DESCRIPTION: SEQ ID NO:8:

TAGCTAACCA CCAACAGCAA GGC                                      23

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:9:

AACTGGCAGC CTGATAGGCA GATTC                                    25

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:10:

GCTCAGCTCC GTTTCGGTTT CACTTCCGGT                                30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:11:

AGCCCCGCAC TTCCACCACC AGCTCCTCCA                                30

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:12:

CGTGGGGTCC TTTTCACCAG CAAG                                     24

(2) INFORMATION FOR SEQ ID NO:13:

(i) SEQUENCE CHARACTERISTICS:
        (A) LENGTH: 23 base pairs
        (B) TYPE: nucleic acid -continued

```
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:13:

AATTATGGAC AGGACTGAAC GTC                                              23

(2) INFORMATION FOR SEQ ID NO:14:

(i) SEQUENCE CHARACTERISTICS:
         (A) LENGTH: 657 amino acids
         (B) TYPE: amino acid
         (D) TOPOLOGY: linear (ii) MOLECULE TYPE: peptide (iii) HYPOTHETICAL: YES (v) FRAGMENT TYPE: C-terminal (xi) SEQUENCE DESCRIPTION: SEQ ID NO:14:

Asp Gly Gly Ala Arg Ala Arg Gly Arg Ala Ala Arg Arg Arg
1               5                  10                  15

Arg Arg Arg Arg Arg Arg Arg Arg Arg Arg Arg Arg Arg Arg Arg
            20                  25                  30

Arg Arg Arg Arg Arg Arg Arg Arg Arg Leu Gly Leu Glu Arg Pro
            35                  40                  45

Gln Pro Thr Ser Arg Gly Arg Ala Pro Gly Ala Ser Arg Ala Glu Glu
    50                  55                  60

Lys Met Glu Glu Leu Val Val Glu Val Arg Gly Ser Asn Gly Ala Phe
65                  70                  75                  80

Tyr Lys Ala Phe Val Lys Asp Val His Glu Asp Ser Ile Thr Val Ala
                85                  90                  95

Phe Glu Asn Asn Trp Gln Pro Asp Arg Gln Ile Pro Phe His Asp Val
                100                 105                 110

Arg Phe Pro Pro Pro Val Gly Tyr Asn Lys Asp Ile Asn Glu Ser Asp
            115                 120                 125

Glu Val Glu Val Tyr Ser Arg Ala Asn Glu Lys Glu Pro Cys Cys Trp
130                 135                 140

Trp Leu Ala Lys Val Arg Met Ile Lys Gly Glu Phe Tyr Val Ile Glu
145                 150                 155                 160

Tyr Ala Ala Cys Asp Ala Thr Tyr Asn Glu Ile Val Thr Ile Glu Arg
                165                 170                 175

Leu Arg Ser Val Asn Pro Asn Lys Pro Ala Thr Lys Asp Thr Phe His
            180                 185                 190

Lys Ile Lys Leu Asp Val Pro Glu Asp Leu Arg Gln Met Cys Ala Lys
            195                 200                 205

Glu Ala Ala His Lys Asp Phe Lys Lys Ala Val Gly Ala Phe Ser Val
        210                 215                 220

Thr Tyr Asp Pro Glu Asn Tyr Gln Leu Val Ile Leu Ser Ile Asn Glu
225                 230                 235                 240

Val Thr Ser Lys Arg Ala His Met Leu Ile Asp Met His Phe Arg Ser
                245                 250                 255

Leu Arg Thr Lys Leu Ser Leu Ile Met Arg Asn Glu Glu Ala Ser Lys
            260                 265                 270
```

-continued

```
Gln Leu Glu Ser Ser Arg Gln Leu Ala Ser Arg Phe His Glu Gln Phe
            275                 280                 285

Ile Val Arg Glu Asp Leu Met Gly Leu Ala Ile Gly Thr His Gly Ala
        290                 295                 300

Asn Ile Gln Gln Ala Arg Lys Val Pro Gly Val Thr Ala Ile Asp Leu
305                 310                 315                 320

Asp Glu Asp Thr Cys Thr Phe His Ile Tyr Gly Glu Asp Gln Asp Ala
                325                 330                 335

Val Lys Lys Ala Arg Ser Phe Leu Glu Phe Ala Glu Asp Val Ile Gln
                340                 345                 350

Val Pro Arg Asn Leu Val Val Ile Gly Lys Asn Gly Lys Leu Ile Gln
            355                 360                 365

Glu Ile Val Asp Lys Ser Gly Val Val Arg Val Arg Ile Glu Ala Glu
        370                 375                 380

Asn Glu Lys Asn Val Pro Gln Glu Glu Glu Ile Met Pro Pro Asn Ser
385                 390                 395                 400

Leu Pro Ser Asn Asn Ser Arg Val Gly Pro Asn Ala Pro Glu Glu Lys
                405                 410                 415

Lys His Leu Asp Ile Lys Glu Asn Ser Thr His Phe Ser Gln Pro Asn
                420                 425                 430

Ser Thr Lys Val Gln Arg Gly Met Val Pro Phe Val Phe Val Gly Thr
            435                 440                 445

Lys Asp Ser Ile Ala Asn Ala Thr Val Leu Leu Asp Tyr His Leu Asn
            450                 455                 460

Tyr Leu Lys Glu Val Asp Gln Leu Arg Leu Glu Arg Leu Gln Ile Asp
465                 470                 475                 480

Glu Gln Leu Arg Gln Ile Gly Ala Ser Ser Arg Pro Pro Pro Asn Arg
                485                 490                 495

Thr Asp Lys Glu Lys Ser Tyr Val Thr Asp Asp Gly Gln Gly Met Gly
            500                 505                 510

Arg Gly Ser Arg Pro Tyr Arg Asn Arg Gly His Gly Arg Arg Gly Pro
            515                 520                 525

Gly Tyr Thr Ser Gly Thr Asn Ser Glu Ala Ser Asn Ala Ser Glu Thr
        530                 535                 540

Glu Ser Asp His Arg Asp Glu Leu Ser Asp Trp Ser Leu Ala Pro Thr
545                 550                 555                 560

Glu Glu Glu Arg Glu Ser Phe Leu Arg Arg Gly Asp Gly Arg Arg Arg
                565                 570                 575

Gly Gly Gly Gly Arg Gly Gln Gly Gly Arg Gly Arg Gly Gly Gly Phe
                580                 585                 590

Lys Gly Asn Asp Asp His Ser Arg Thr Asp Asn Arg Pro Arg Asn Pro
            595                 600                 605

Arg Glu Ala Lys Gly Arg Thr Thr Asp Gly Ser Leu Gln Asn Thr Ser
        610                 615                 620

Ser Glu Gly Ser Arg Leu Arg Thr Gly Lys Asp Arg Asn Gln Lys Lys
625                 630                 635                 640

Glu Lys Pro Asp Ser Val Asp Gly Gln Gln Pro Leu Val Asn Gly Val
                645                 650                 655

Pro
```

DIAGNOSIS OF THE FRAGILE X SYNDROME

This invention was supported by the National Institutes of Health, under grant number LTD 20521. The government may have certain rights under this application.

This invention was partially supported by grants from the United States Government, The government has certain rights in the invention.

FIELD OF THE INVENTION

This invention relates to the field of molecular diagnosis of the fragile X syndrome.

BACKGROUND

The fragile X syndrome is the most frequently encountered form of inherited mental retardation in humans and has a prevalence estimated to be 1/1250 males. The fragile X syndrome segregates as an X-linked dominant disorder with reduced penetrance. Either sex when carrying the fragile X mutation may exhibit mental deficiency. It has been shown that approximately 30% of carrier females are penetrant and that 20% of males carrying the fragile X chromosome are normal but may transmit the disorder and have fully penetrant grandsons. In addition to the mental retardation which is variable in severity, penetrant males exhibit additional phenotypic involvement including macroorchidism and distinctive facies. Since fully penetrant males rarely reproduce, it has been suggested that the frequency of new mutations of the fragile X site may be as high as 1/3000 germ cells to maintain the population frequency.

The fragile X syndrome, as implied by its name, is associated with a fragile site expressed as an isochromatid gap in the metaphase chromosome at map position Xq 27.3. The fragile X site is induced by cell culture conditions which perturb deoxypyrimidine pools and is rarely observed in greater than 50% of the metaphase spreads. Neither the molecular nature of the fragile X site, nor its relationship to the gene responsible for the clinical expression of the syndrome is understood. However, based upon genetic linkage studies, as well as in situ hybridizations, the fragile X site and its associated gene are tightly linked if not coincident.

The present application provides a new procedure for detecting the fragile X site at the molecular level. It provides a molecular method for the diagnosis of the fragile X syndrome, describes a unique open reading sequence at the suspected gene locus and provides probes to the fragile X region.

SUMMARY OF THE INVENTION

An object of the present invention is a method for diagnosing fragile X syndrome.

A further object of the present invention is the provision of a sequence of the FMR-1 gene.

An additional object of the present invention is a method of detecting the fragile X syndrome by measuring the mRNA or protein from the FMR-1 gene.

Thus in accomplishing the foregoing objects there is provided in accordance with one aspect of the present invention as a composition of matter, a 3.8 kb cDNA clone containing the FMR-1 gene. A further aspect is a 4242 bp genomic DNA sequence containing at least a fraction of the FMR-1 gene.

A further embodiment of the present invention is a group of cosmid probes for the selection of the FMR-1 gene in the fragile X syndrome.

An additional embodiment of the present invention is a method of detecting fragile X syndrome comprising the steps of digesting DNA from an individual to be tested with a restriction endonuclease and detecting the restriction fragment length polymorphism with hybridization to probes within the fragile X locus and southern blot analysis. In a preferred embodiment of the present invention, the probe is pE5.1 and the restriction endonucleases are selected from the group consisting of EcoR I, Pst I, Xho I and BssH II.

Alternate embodiments of the present invention include detecting the fragile X syndrome by measuring the expression of the FMR-1 gene either as the amount of mRNA expressed or as the amount of FMR-1 protein produced. Another embodiment of the present invention includes a method of detecting X-linked disease comprising the steps of detecting variation in the $(CGG)_n$ repeat at the 5' end of the FMR-1 gene by measuring the length of the repeat, wherein n for normal ranges between 16 and 30 and n for X-linked disease is greater than 30. A variety of methods are available to detect the dosage measurements of the repeat. These procedures can be selected from the group consisting of visual examination, densitometry measurement, quantitative radioactivity and quantitative fluorescence as well as pulsed field gel electrophresis and fluorescence in situ hybridization.

Other and further objects, features and advantages will be apparent and eventually more readily understood from a reading of the following specification and by reference to the accompanying drawings forming a part thereof, wherein examples of the presently preferred embodiments of the invention are given for the purpose of the disclosure.

Figure 1:
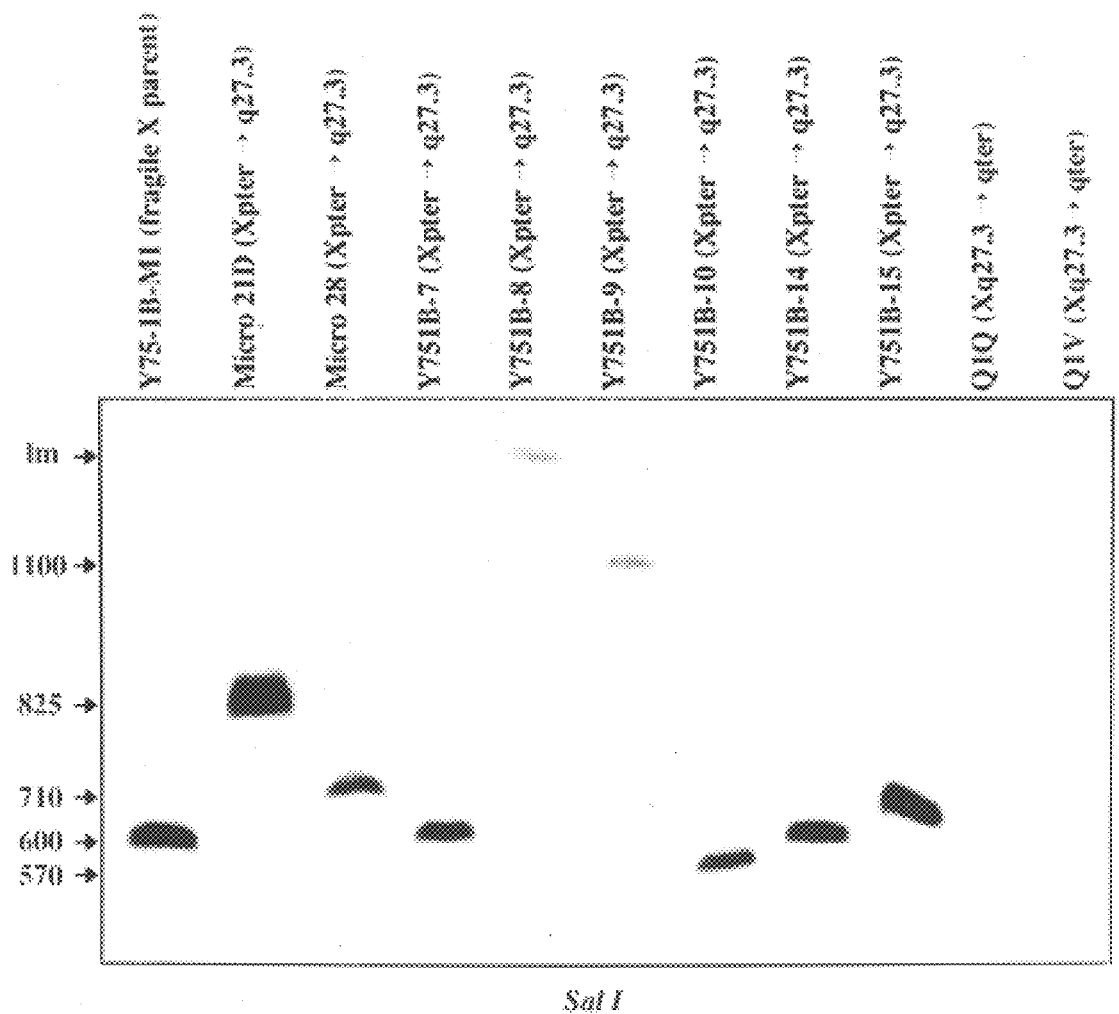
FIG. 1 is a Southern blot analysis of pulsed field gel resolved Sal I digested DNA of proximal translocation hybrids probed with p46-1.1.

The drawings and figures are not necessarily to scale and certain features mentioned may be exaggerated in scale or shown in schematic form in the interest of clarity and conciseness.

DETAILED DESCRIPTION OF THE INVENTION

It will be readily apparent to one skilled in the art that variations, substitutions and modifications may be made to the invention disclosed herein without departing from the scope and the spirit of the invention.

Each sample to be tested herein for the fragile X site is derived from genomic DNA, mRNA or protein. The source of the genomic DNA to be tested can be any medical specimen which contains DNA. Some examples of medical specimen include blood, semen, vaginal swabs, buccal mouthwash, tissue, hair and mixture of body fluids. As used herein the term "polymerase chain reaction" or "PCR" refers to the PCR procedure described in the patents to *Mullis*, et al., U.S. Pat. Nos. 4,683,195 and 4,683,202. The procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

As used herein fluorescence in situ hybridization or "FISH" refers to the procedure described in Wotta, et al., Am. J. of Human Genetics, 46, 95–106 (1988) and Kievits, et al., Cytogenet. Cell Genet., 53134–136 (1990). The procedure basically involves the steps of preparing interphase or metaphase spreads from cells of peripheral blood lymphocytes and hybridizing labeled probes to the interphase or metaphase spreads. Using probes with mixed labels allows visualization of space, order and distance between hybridization sites. After hybridization the labels are examined to determine the order and distance between the hybridization sites.

As used herein, the term "pulsed field gel electrophoresis" or "PFGE" refers to a procedure described by Schwartz, et al., Cold Springs Harbor Symposium, Quantitative Biology, 47:189–195 (1982). The procedure basically comprises running a standard electrophoresis gel (agarose, polyacrylamide or other gel known to those skilled in the art) under pulsing conditions. One skilled in the art recognizes that the strength of the field as well the direction of the field is pulsed and rotated in order to separate megabase DNA molecules. Current commercial systems are computer controlled and select the strength, direction and time of pulse depending on the molecular weight of DNA to be separated.

One embodiment of the present invention as a composition of matter is a 3.8 kb cDNA clone (SEQ. ID. No. 1) containing the FMR-1 gene.

Another embodiment of the present invention is a 4242 bp genomic DNA (SEQ. ID. No. 2). This DNA is a sequence of pE5.1 from the distal Eco RI site containing the fragile X region. Further, there is a 229 bp genomic DNA (SEQ. ID. No. 3) of pE5.1 from the proximal Eco RI site.

One embodiment of the present invention is a method of detecting Fragile X syndrome comprising the steps of digesting DNA from an individual to be tested with a restriction endonuclease and detecting the restriction fragment length to polymorphism (RFLP) with hybridization to probes within the fragile X locus and southern blot analysis. One skilled in the art will readily recognize that a variety of restriction endonucleases can be used. In the preferred embodiment the restriction endonuclease is selected from the group consisting of EcoR I, Pst I, Xho I and BssH II.

In the method of detection, it is found that the probe pE 5.1 is used in the preferred embodiment. Again, one skilled in the art readily recognizes that other probes or fractions of the probe pE5.1 which hybridize to the unique fragment lengths can be used.

An alternative method for detecting the Fragile X syndrome comprises the step of measuring the expression of the FMR-1 gene. The FMR-1 gene can be measured by either measuring the amount of mRNA expressed or by measuring the amount of FMR-1 protein.

When measuring the amount of mRNA expressed, the amount of mRNA is determined by the steps of extracting RNA from any tissue source including fibroblast and lymphoblastoid cell lines of the individuals to be tested. From the RNA of FMR-1, a cDNA is prepared. From RNA of a control gene a cDNA is prepared. Then quantification is achieved by comparing the amount of mRNA from FMR-1 with the mRNA from the controlled gene. In the preferred embodiment, the quantification step includes PCR analysis of the FMR-1 cDNA and PCR analysis of the control gene cDNA. The PCR products are electrophoresed and ethidium bromide stained. The products are then quantified by comparing the FMR-1 product versus the control gene product after the ethidium bromide staining. The oligonucleotide primers for the fragile X site are SEQ. ID. No. 8 and SEQ. ID. No. 9. One example of the control gene is HPRT and the oligonucleotides are SEQ. ID. No. 12 and SEQ. ID. No. 13.

When measuring the amount of FMR-1 protein produced, one can use any of the variety of methods known in the art to detect proteins, including monoclonal antibodies, polyclonal antibodies and protein assays. In the preferred embodiment, the antibodies detect SEQ. ID. No. 14.

The methods described herein can also be used to detect X-linked disease. The method comprises the steps of detecting variation of the $(CGG)_n$ repeat found at the 5' end of the FMR-1 gene by measuring the length of the repeat wherein n (number of repeats) for normal is in the range between 16 and 30 and n for X-linked diseases is in the range of greater than 30. In the case of Fragile X, n is usually at least twice the range of normal. Types of disease which can be detected are X-linked mental retardation both of fragile X and non-fragile X type, X linked manic depressive disease, TKCR syndrome and Martin-Bell syndrome.

The method of dosage compensation by measuring the amount or length of the repeat can be done by using FISH. In the FISH method, the repetitive sequence can be used as a probe to distinguish between normal and fragile X syndrome simply by the presence or absence of a signal to the repetitive sequence. In this case, the application of the repeat sequence provides a sufficiently large target for the hybridization. Thus, it is possible that very sensitive FISH might detect transmitting males (with 50–100 copies of the CGG) even though these would be lost to routine microscopy and detection. Although FISH is usually applied to metaphase nuclei, in the present invention it is applicable to both metaphase and interphase for the detection of X-linked disease.

Alternate methods to measure the dosage measurement of the repeat can include visual examination, densitometry measurement, quantitative radioactivity and quantitative fluorescence.

In one embodiment the size of the repeat is determined by dosage measurements of Southern blotting analysis of restriction enzyme digests with probes contained within the FMR-1 gene region.

It is also known that the method of PFGE can be used to detect variation at the fragile X locus.

In another embodiment the variation of the (CGG)n repeat is measured by PCR. In this method the oligonucleotide primers are SEQ. ID. No. 10 and SEQ. ID. No. 11.

Figure 4:
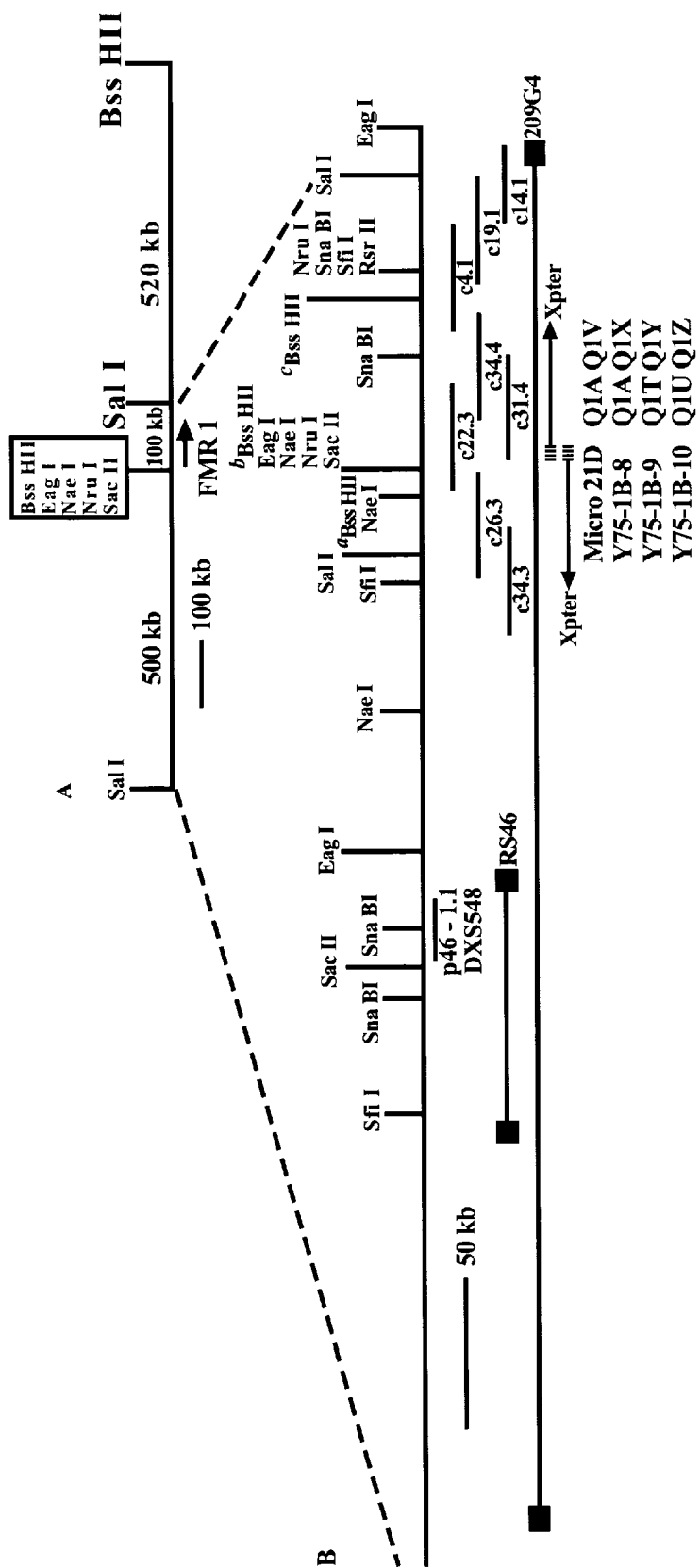
FIGS. 4A and 4B comprise a physical map of the fragile X region of a genomic and YAC 209G4 DNA.

Another embodiment of the present invention is the cosmid probes shown in in FIG. 4. These cosmid probes can be selected from the group consisting of C 22.3, C 34.4, C 31.4, C 4.1, C 34.3, C 26.3 C 19.1 and C14. 1. These cosmid clones are Sau 3A digests of the YAC 209G4. These digests were cloned into p2CpG. This results in inserts from 35–45 Kb. The ends are defined by their positions on the map of FIG. 4. These cosmid probes overlap the range in which the FMR-1 gene is located.

In detecting the fragile X sites the length of CA polymorphisms at the fragile X site can be measured by performing a PCR assay and measuring the length of the amplified products. In the PCR assay, the oligonucleotide primers are SEQ. ID. No. 6 and SEQ. ID. No. 7.

The following examples are offered by way of illustration and are not intended to limit the invention in any manner. In the examples all percentages are by weight, if for solids and by volumes, if for liquids and all temperatures are in degrees Celsius unless otherwise noted.

EXAMPLE 1

Pulsed Field Gel Electrophoresis

Southern blot analysis of genomic DNA or YAC DNA resolved by PFGE was performed essentially as described (Smith, et al., Pulsed-field gel electrophoresis and the technology of large DNA molecules. In Genome Analysis: A Practical Approach; Oxford:IRB Press, pp.41–72, 1988). In this procedure, trypsinized and washed mammalian cells were suspended in molten agarose (final concentration 0.5% wt/vol; Baker) prepared in SE buffer (75 mM NaCL, 25 mM EDTA, pH 8.0) at a final concentration of $1.5 \times 10^7$ cells/mi. Chromosomal DNAs were isolated from YAC clones. Yeast cells from a 10 ml saturated culture were harvested, rinsed once in 50 mM EDTA, pH 8.0 and recovered in 0.5 ml SBE-zymolase (1 M sorbitol, 25 mM EDTA pH 8.0, 14 mM 2-mercaptoethanol, 1 mg/ml zymolase [1CN]). 0.5 ml 1% Seaplaque agarose (FMC) in SBE (without zymolase) was added and the suspension transferred to plug molds. Spheroplast generation (for yeast cells) was for 5 hours to overnight in SBE-zymolase. Cell lysis (mammalian or yeast cells) was for 2 days in ESP (0.5 M EDTA, pH 9.5, 1% N-laurolsarcosine, 1 mg/ml proteinase K) at 50° C. Restriction endonuclease digestion was performed using the manufacturer's recommended buffers and conditions with a 50 μl plug slice in 250 μl of buffer containing 50 units of enzyme. For double digests, the plugs were rinsed and equilibrated, following digestion with the first enzyme, with the second buffer several times prior to digestion with the second enzyme. PFGE was carried out on a Bio-Rad Contour-Clamped Homogeneous Electric Field (CHEF) DRII apparatus through 1% agarose (BRL) at 200 V and 14° C. in 0.5×TBE buffer (45 mM Tris-borate, 1 mM EDTA). For resolution of fragments of ≈200–1200 kb, switch time was 60 see for 17 hrs followed by 90 sec for 10 hrs; for resolution of fragments ≈10–500 kb, the switch times were ramped from 5 sec to 50 see over 27 hrs. Southern blotting and hybridization were carried out as described in the art with the exception that acid depurination in 0.25 M HCl was allowed to proceed 20 min for pulsed-field gels. Radiolabeled probes were synthesized by random priming from 50 ng gel purified fragments except when intact cosmids were used which were nick translated (Boehringer Mannheim kit; following manufacturer's recommendations). For genomic probes containing repetitive elements, repeat suppression was accomplished by preassociation with 1–3 mg of sonicated human placental DNA in 100–300 μl of 5×SSC (1×SSC is 150 mM NaCl, 15 mM NaCitrate, pH 7.0) for 3–10 min at 65° C. prior to the addition to the filter. Washing was carried out to a final stringency wash of 0.2×SSC for 15 min at 65° C. prior to autoradiography. S. cerevisiae strain YNN295 chromosomes (BioRad), concatamers of phage lambda (BioRad) or high molecular weight markers (BRL) were used as size standards.

EXAMPLE 2

PCR Analysis of DXS548 Alleles

Amplification was carried out on 0.2–0.5 μg of genomic DNA in a 10 μl total reaction containing 0.25 mM dNTPs, 40 ng of primers SEQ. ID. NO. 6 and SEQ. ID. No. 7, and 0.25 units of Taq polymerase in a buffer of 10 mM Tris-HCl, 50 mM KCl, 12 mM MgCl and 0.01% gelatin. Twenty three cycles of PCR were carried out in the following fashion; 3 cycles of 1 min each at 97° C., 62° C. annealing and 72° C. extension followed by 20 additional cycles with the annealing temperature lowered to 55° C. The reaction volume was then increased to 50 μl with the same reaction components and concentrations except that one primer was 5' end-labelled with $Y^{32}P$-ATP. PCR was continued for 10 cycles of 1 min each at 95° C. denaturation, 62° C. annealing and 72° C. extension. PCR products were analyzed by electrophoresis of 2 μl of reaction through a 40 cm 6% polyacrylamide denaturing sequencing gel for approximately 2.25 hrs. The gel was dried without fixing and exposed to X-ray film overnight at room temperature.

EXAMPLE 3

Cosmid Library Construction of YAC 209G4

Agarose plugs (0.5% SeaPlaque FMC) containing 5–10 μg of yeast DNA were prepared. 100 μl blocks of DNA were equilibrated on ice in 0.5 ml of Mbo I digestion buffer, containing 0.1 mg/ml bovine serum albumin (BSA, MB grade; Boehringer Mannheim). After 2–3 hrs, the buffer was replaced by 150 μl of fresh buffer to which Mbo I was added (0.0001–0.0007 units). Following overnight incubation on ice, digestion was carried out for 40 min at 37° C. The agarose blocks were melted, the DNA dephosphorylated with 1 unit calf intestinal alkaline phosphatase (Beohringer Mannheim), and treated with 2.5 units of agarase (Calbiochem). The solution was extracted twice with phenol/chloroform, once with chloroform, the DNA precipitated with ethanol and dissolved in 10 mM Tris, 0.1 mM EDTA (pH 7.4) at a concentration of 500 ng/μl. 250 ng of DNA was ligated to 500 ng of Bst Bl (dephosphorylated) and Bam HI digested vector (p2CpG). Ligation and packaging was carried out according to standard procedures. Cosmids containing human inserts were selected by hybridizing with human specific Alu-repeat probe. These cosmids can be seen in FIG. 4.

EXAMPLE 4

YAC and Cosmid Subcloning

YACs were subcloned following isolation of the intact chromosome by preparative PFGE and EcoR I digestion of the DNA in molten agarose (Seaplaque; FMC). Fragments were phenol/chloroform extracted, ethanol precipitated, recovered and ligated into EcoR I cut, dephosphorylated, lambda ZAP II arms according to manufacturer's recommendations (Stratagene). Cosmids were subcloned following an alkaline lysis isolation and EcoR I digestion. Fragments were phenol/chloroform extracted and ethanol precipitated prior to ligation into lambda ZAP II arms as with YAC fragments. In the case of both cosmids and YACs, 75 ng EcoR I fragments were ligated to 1 ug vector arms. Selected phage were converted into pBluescript II SK-clones following in vivo excision of plasmid with insert according to manufacturer's guidelines.

EXAMPLE 5 cDNA Library Screening

A human fetal brain lambda gt11 cDNA library (Clonetech, Palo Alto, Calif.) of $1.3 \times 10^6$ independent clones with insert lengths of 0.7–4.0 kb was used. The library was plated on 15 cm plates at a density of 50,000 pfu per dish using strain LE392. Filter lifts were prepared according to standard techniques and the library screened with cosmid DNA hexanucleotide labelled with $^{32}$P-dATP and $^{32}$P-dCTP. The labelled DNA was first prehybridized with 100 µg of total sheared human genomic DNA and 100 µg cosmid vector DNA in 5×SSC at 65° C. for 2 hrs. Following hybridization for 16 hrs, the filters were washed to a stringency of 0.1×SSC. The filters were exposed to Fuji film with intensifying screens for 2 days at −80° C.

EXAMPLE 6

Fluorescent In Situ Hybridization

In situ hybridizations of total YAC-containing yeast DNA and cosmids were performed. Fragile X expression was induced by 96 hr culturing of lymphocytes (PHA stimulated from a male fragile X patient) in medium TC199 (Gibco) supplemented with 10% bovine fetal calf serum and, for the last 24 hrs, 10 µg/ml methotrexate (Lederle). Chromosomes were prepared on slides using standard techniques.

Slides were washed with PBS and incubated for 1 hr at 37° C. in RNase A (100 µg/ml) in 2×SSC. The slides were then incubated 10 min with pepsin (Serva; 0.1 mg/ml in 0.01 N HCL), fixed in 1% (vol/vol in PBS, 50 mM MgCl$_2$) formaldehyde (Merck) and dehydrated in cold ethanol. Biotinylated total yeast and cosmid DNA were preannealed for 1–4 hrs in the presence of sonicated human genomic DNA and hybridized to the chromosomes overnight using 150 ng (yeast) or 40 ng (cosmid) of probe in 10 µl of 50% formamide, 2×SSC, 10% dextran sulfate under an 18 mm$^2$ coverslip sealed with rubber cement. In some experiments, 2 ng/µl pBamX5, a human repetitive sequence detecting the pericentromeric region of the human X, was separately denatured and added to the hybridization solution.

The signals were amplified by two layers of avidin-FITC (Vector) and one layer of biotinylated goat anti-avidin (Vector). The slides were then washed with PBS and mounted in antifade medium of 2% DABCO in glycerol containing propidium iodide (0.03 µg/ml). Microscopic analysis was performed with a Leitz Aristoplan microscope with FITC (K3 block) and DAPI (A block) detection. Photographs were made using Ektachrome 400 (Kodak) daylight slide film.

EXAMPLE 7

Northern Blot Analysis

Total RNA was extracted using guanidinium isothiocyanate followed by centrifugation through cesium chloride. Poly(A)$^+$ RNA was selected by passage through oligo(dT) cellulose. Human brain, liver, and fetal poly(A) RNA was purchased from Clontech Laboratories (Palo Alto, Calif.).

Five µg of poly(A) containing RNA or 25 µg of total RNA were precipitated and dissolved in 20 µl of 50% (vol/vol) formaldehyde and 1×MEN (20 mM MOPS, pH 6.8, 5 mM sodium acetate, 1 mM EDTA) and incubated for 10 min at 60° C.; 5 µl of dye marker (50% sucrose, 0.5% bromophenolblue) was added and the samples were loaded on a formaldehyde-agarose gel. Electrophoresis was carried out for 3 hrs. at 100 V and the gel then soaked for 30 min in 20×SSC and blotted onto a nitrocellulose or nylon (GeneScreen Plus, Dupont) overnight in 10×SSC (Thomas, 1980). The RNA was fixed to the membranes by baking under vacuum for 2 hrs at 80° C. The membranes were prehybridized in 50% formamide, 5×Denhart's, 50 mM sodium phosphate, pH 6.8, 10% dextran sulfate and 100 µg of denatured salmon sperm DNA at 42° C. for 2–4 hrs. Hybridization with the probe was for 16–20 hrs at 42° C. in the above buffer. Filters were washed with 3×SSC, 0.1% SDS at 50° C. and then the SSC concentration was lowered according to the level of background, with a final wash in 0.1×SSC, 0.1% SDS.

EXAMPLE 8

RT-PCR Quantitation of the FMR-1 Transcript

A PCR based test is devised in which the transcription product from the FMR-1 gene is quantitated with respect to an internal control (HPRT gene), in RNA samples from Fragile X and normal cell lines. In this method the total RNA was extracted from lymphoblastoid cell lines derived from Fragile X affected individuals and normal controls. The cDNA synthesis was performed in vitro from 5 µg of total RNA using oligo-dT and random primers via a reverse transcriptase reaction. Then PCR from single stranded cDNA was carried out using primers specific for the HPRT cCNA (SEQ. ID. Nos. 12 and 13) and primers specific for the FMR-1 cDNA (SEQ. ID. Nos. 8 and 9). The PCR conditions were as follows: 94° C., 1 min; 55° C. 1 min; 72° C. 1 min 45 sec; for 28 cycles and 7 min final extension at 72° C. The PCR products were run on an ABI Horizontal Electrophoresis device, by which the ethidium bromide stained products of each gene were exactly quantitated with respect to each other. Quantitative variations in the expression of the FMR-1 gene in Fragile X patients derived cell lines was then monitored.

EXAMPLE 9

Isolation of YACs Spanning the Fragile X Translocation Breakpoints

Through regional mapping of YAC clones containing DNA inserts derived from the distal human Xq, an 80 kb YAC (RS46) was found to map within Xq27.3 proximal to the fragile X-associated hybrid breakpoints. A 4.0 kb subclone (p46-1.1) of RS46 identified a normal 600 kb Sal I fragment on PFGE that was altered in size in 6 of 8 proximal translocation hybrids (FIG. 1). In FIG. 1, Y75-1B-M1 is a somatic cell hybrid containing the intact fragile X chromosome from which all other hybrids were derived. Lanes 2–9 are proximal translocation hybrids containing centric human Xpter→q27.3 translocated to different rodent chromosome arms. Q1Q and Q1V are distal translocation hybrids containing human Xq27.3→qter translocated to different centric rodent chromosome. The distal translocation hybrids have lost the human sequence detected by p46-1.1. Hybrids Y751B-7 and Y751B-14 show the same 600 kb Sal I fragment as the parental hybrid, however all other proximal translocation hybrids show variant bands indicating that probe p46-1.1 detects a sequence within 600 kb of these translocation breakpoints.

PFGE analyses of these hybrids, with more distant X-linked probes, showed identical band sizes and therefore similar methylation patterns as might be expected since the hybrids were all derived from the same parental fragile X somatic cell hybrid (Y75-1B-M1). These data suggest that in 75% of the proximal translocation hybrids, the human breakpoint is within the 600 kb Sal I fragment observed in the parental, intact fragile X hybrid. In the translocation hybrids, the distal human Sal I site is lost and replaced by heterologous translocations containing different rodent Sal I sites.

Figure 2:
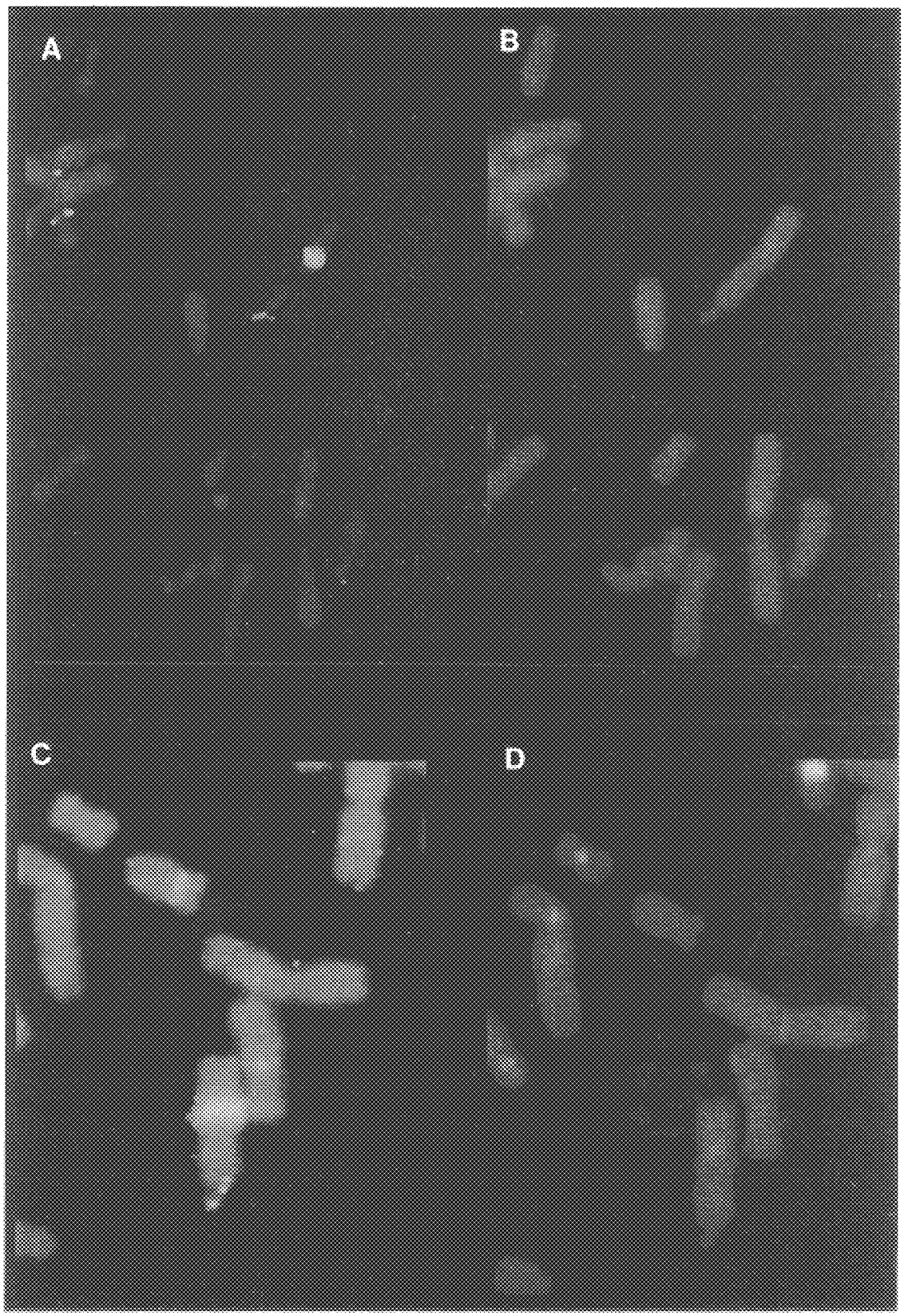
FIGS. 2A–2D show fluorescent in situ hybridization of YAC 209G4 and cosmids to the fragile X site at Xq 27.3 of an affected male patient.

Since YAC RS46 does not hybridize to the DNA of the distal translocation hybrids and therefore does not cross these translocation breakpoints, additional YACs were sought of this region. A YAC library developed at the Human Polymorphism Study Center (CEPH) was screened using RS46 specific oligonucleotide primers SEQ. ID. Nos. 4 and 5 or SEQ. ID. Nos. 6 and 7. A YAC of 475 kb (209G4) was identified which completely overlaps YAC RS46 and includes sequences distal to the proximal translocation breakpoints which are present in 13 or 14 distal translocation breakpoints. YAC 209G4 encompasses 86% (19/22) of both the proximal and distal translocation breakpoints and thus identifies a fragile X-associated breakpoint cluster region. In situ hybridization using YAC 209G4 showed localization to the expressed fragile X site (FIG. 2). In FIG. 2, panel A represents the localization of YAC 209G4 to the expressed fragile X site. The centrometric signal is due to pBamX5, indicating the human X chromosome with slight hybridization to acrocentric chromosomes; Panel B shows a DAPI stained spread of panel A showing the expressed fragile X site; Panel C shows localization of cosmid 7.1 to the fragile X region; and finally, panel D shows localization of cosmid 22.3 to the fragile X region.

The signal includes both flanking boundaries of the isochromatid gap of the fragile site as well as the gap itself, suggesting the presence of uncondensed DNA within the fragile site and indicating that YAC 209G4 includes this region.

Figure 3:
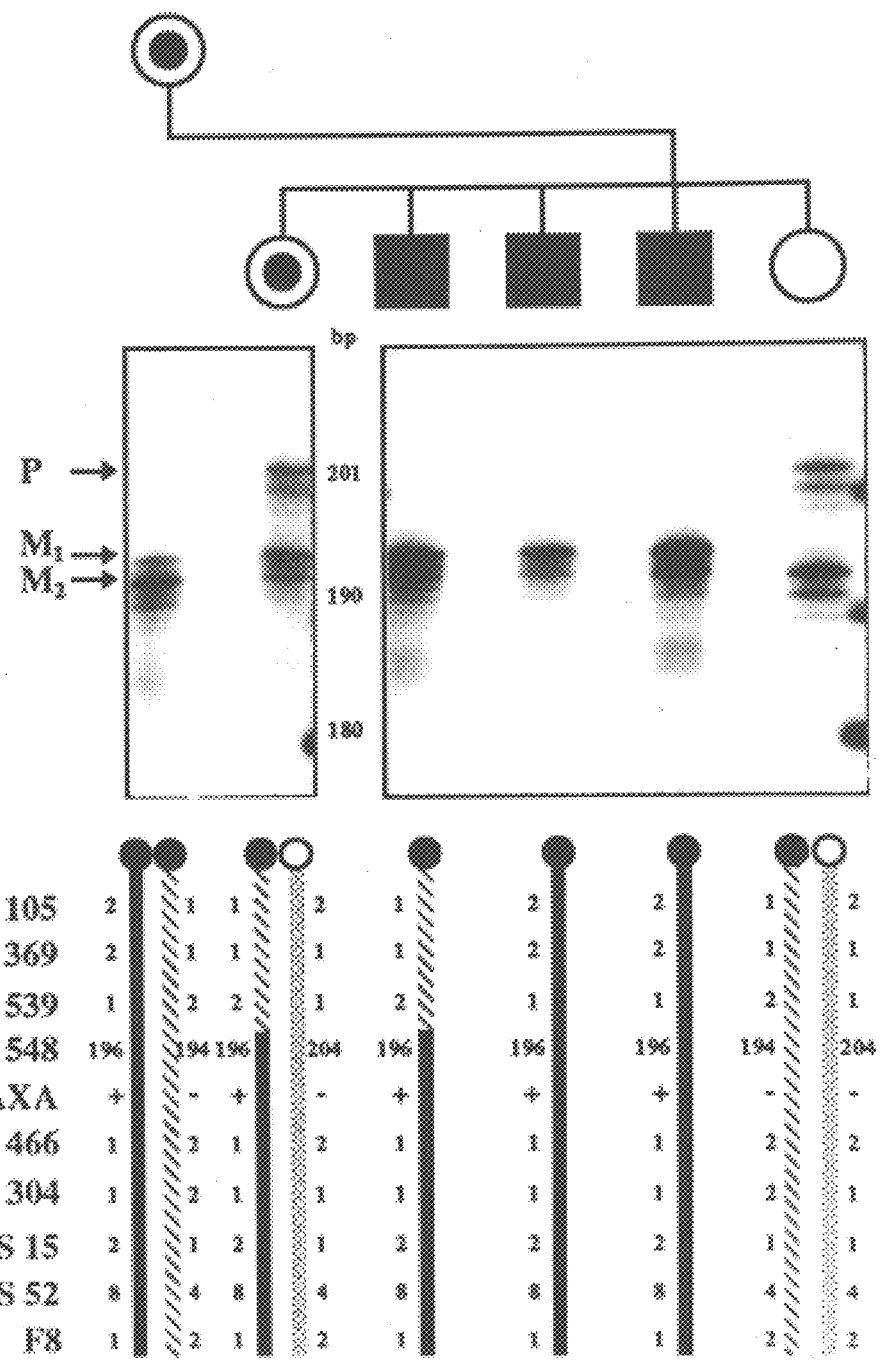
FIG. 3 is a PCR analysis of DXS548 alleles in a fragile X family with recombinant individuals.

The close proximity of these YACs to the fragile X locus was independently supported by genetic linkage studies between a polymorphism identified in YAC RS46 and the fragile X locus. DXS548 is a dinucleotide repeat which reveals 9 alleles of variable length that are informative in >80% of fragile X families. In highly selected families previously shown to have crossovers with tightly linked flanking markers, DXS548 cosegregated, without recombination, with the fragile X locus (lod score of 6.95 at Θ=0). As shown in FIG. 3, a carrier daughter and affected son are recombinant between the fragile X locus (FRAXA) and proximal markers DXS 539 (probe JH89) and DXS 369 (probe RN1) which map approximately 5 cM proximal to FRAXA with lod scores >40. The carrier mother shows two DXS 548 alleles at 196 and 194 bp (M1 and M2, respectively). The paternal 204 allele of the father is seen in the carrier daughter (II-1) who also inherited the maternal 196 bp allele. All three affected males inherited the 196 bp maternal allele (compare with the 194 allele of the normal daughter (II-5). The carrier daughter (II-1) and affected son (II-2) are both recombinants between proximal markers DXS 150, DXS 369 and DXS 539. However, these individuals are non-recombinant with DXS 548, placing this locus to the crossovers closer to the fragile X locus. Therefore, DXS 548 positions YACs RS46 and 209G4 near the mutation responsible for the clinical phenotype of the fragile X syndrome.

EXAMPLE 10

Physical Map of YAC 209 G4

A physical map of YAC 209G4 and of the corresponding genomic region was developed and is shown in FIG. 4. In FIG. 4(A), the physical map of the fragile X chromosome in the vicinity of the Fragile X locus is shown. The Sal I sites which give rise to the 600 kb fragment seen in hybrid Y75-1B-M1 probed with p46-1.1 and the normal 620 kg BssH II fragment observed in normal X chromosomes can be seen. The sites within the box are those previously shown to be methylated on the fragile X chromosome. The position and orientation of FMR-1 is shown.

In FIG. 4(B), a higher resolution physical map derived from both YAC inserts and genomic DNA is shown. Probe p46-1.1 and the DXS 548 loci are shown as are the positions of cDNAs and cosmids. YACs RS46 and 209G4 are shown below in alignment with the map (Hatched boxes indicate YAC vector sequences). The positions of the translocation breakpoints are shown as well as the orientation of the map relative to the X chromosome telomeres.

A CpG-island containing 5 infrequent-cleaving restriction endonuclease sites was identified 150 kb distal to CSX 548. This CpG-island appears hypermethylated on the fragile X chromosome. It is known in the art that there is an absence of a normal 620 kb BssH II fragment (FIG. 4A) in patients and most carriers of the fragile X syndrome. The absence of the fragment appears to be due to the methylation (and therefore resistance to cleavage) of the BssH II site (b in FIG. 4B) leading to a very large band which fails to resolve on PFGE. Since CpG-islands often are found 5' to mammalian genes and since methylation of such islands may influence expression of associated genes, it is possible a gene may reside nearby this fragile X-related CpG-island and its expression (or lack of) may be responsible for at least a portion of the fragile X phenotype.

EXAMPLE 11

Cosmid Contig Surrounding the Fragile X-Related CpG Island and Breakpoint Cluster Region To characterize the region surrounding the CpG-island, a cosmid library was constructed from the yeast clone harboring YAC 209G4 and cosmids containing human DNA were identified by hybridization to human-specific repetitive elements. In situ hybridization with several human cosmids showed signals in (FIG. 2C) and on the edge (FIG. 2D) of the fragile X gap. A four cosmid contig was identified which spans the fragile X-related CpG island (FIG. 4B) from BssH II site a (cosmid 22.3) through BssH II site c (cosmid 4.1).

Figure 5:
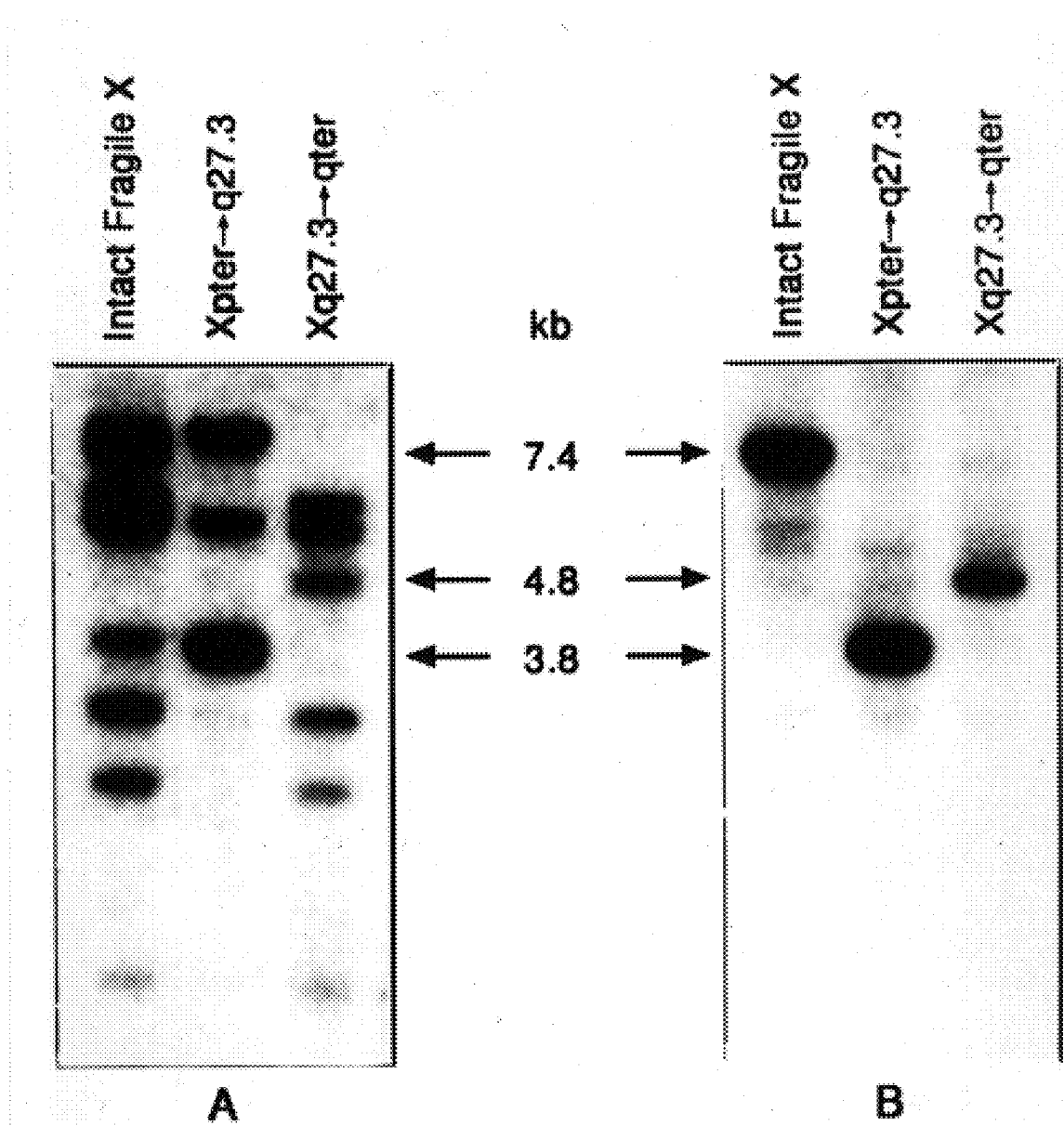
FIGS. 5A and 5B depict a Southern blot analysis of fragile X associated translocation breakpoints. In (A) the Southern blot is hybridized with cosmid 22.3 and in (B) the same filter is hybridized with pE5.1.

Cosmid 22.3 was found to include the breakpoints of 11 of 16 tested translocation hybrids (4/5 proximal translocations and 7/11 distal translocations; all 16 breakpoints map within YAC 209G4). As shown in FIG. 5A, nine bands (including doublet bands at 5.6 and 5.5 kb), surveying approximately 44 kb of genomic DNA, are observed on Southern analysis of EcoR I digested DNA of the intact fragile X hybrid (Y75-1B-M1) following hybridization with radiolabeled and preannealed cosmid 22.3. Of these nine bands, three are present in the distal Q1X (with a novel 4.8 kb junctional fragment). The 7.4 kb band of the intact X hybrid Y75-1B-M1 is absent in both translocation hybrids indicating that both breakpoints fall within this interval. The other nine hybrids all exhibited patterns similar to either micro21D or Q1X, with distinct junctional fragments allowing identification of a fragile X-associated breakpoint cluster region (FXBCR) with this 7.4 kb fragment.

Figure 6:
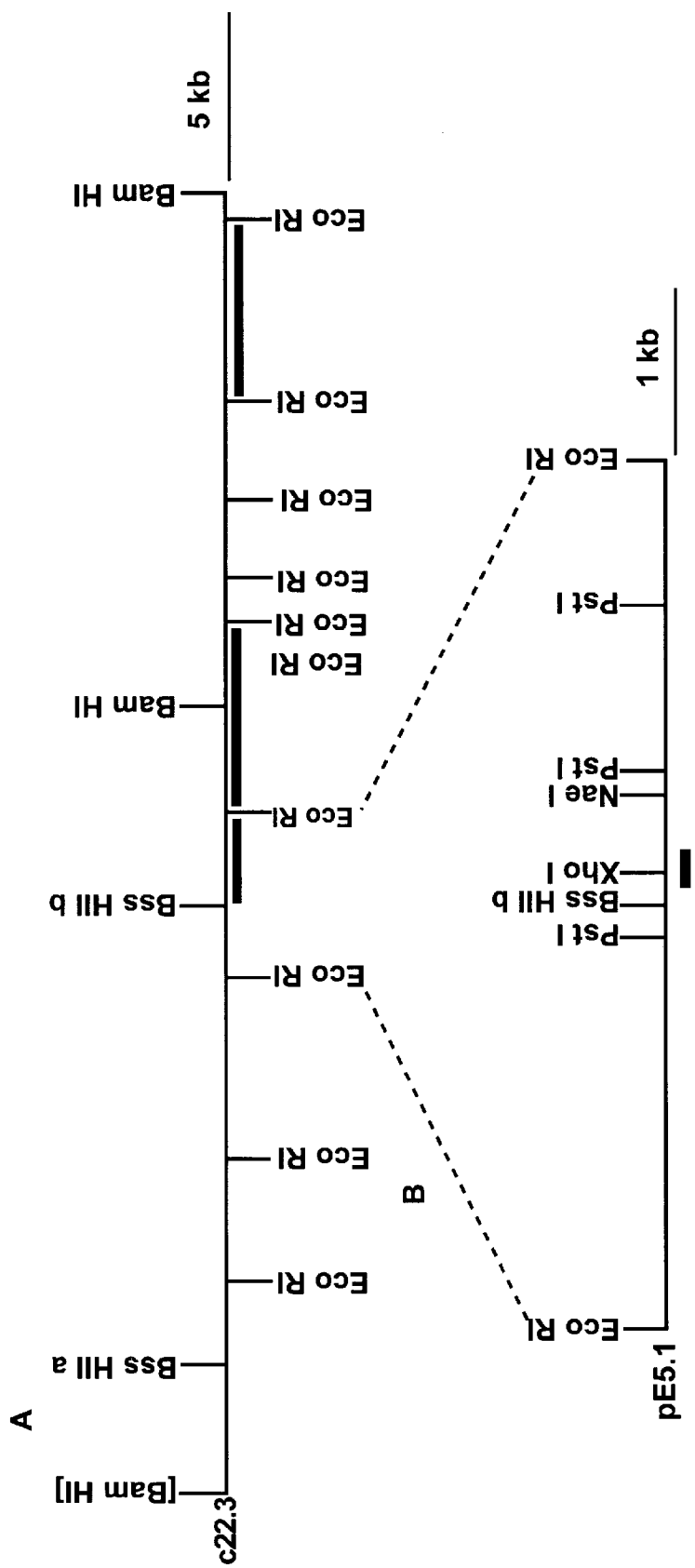
FIGS. 6A and 6B comprise a restriction map of cosmid 22.3 and pE5.1. In (A) is cosmid 22.3 showing BssH II sites a and b as well as EcoR I and BamH I sites. The BamH I site in parentheses was destroyed during cloning. The solid lines below the map show fragments which hybridize to cDNAs BC72 and BC22. In (B) is the map of the cloned 5.1 kb EcoR I fragment of cosmid 22.3 (pE5.1). The solid line below the map shows the position of the FMR-1 exonic sequence which contains the Xho I site.

The 7.4 kb EcoR I fragment observed above on the fragile X chromosome was not observed in restriction digests of the overlapping cosmids 22.3 and 31.4. However, comparison of the cosmid restriction maps with the EcoR I fragments detected by c22.3 show a 5.1 kb fragment in the cosmids that is absent in Y75-1B-M1 and replaced by the 7.4 kb fragment. As shown in FIG. 6A, this 5.1 kb fragment contains the BssH II site b exhibiting fragile X specific hypermethylation. This fragment was subcloned from c31.4 and used to analyze hybrid breakpoints. As shown in FIG. 5B, the 5.1 kb fragment (pE5.1; FIG. 6B) hybridizes specifically to the 7.4 kb EcoR I fragment of the fragile X chromosome and clearly shows the junctional fragments in micro21D and Q1X. Thus a fragment length difference exists between the normal DNA used to construct YAC 209G4 and the fragile X chromosome of hybrid Y75-1B-M1, and this fragment identifies the FXBCR.

EXAMPLE 12

Fragile X Breakpoint Cluster Region Rearranged in Fragile X Patients

Figure 7:
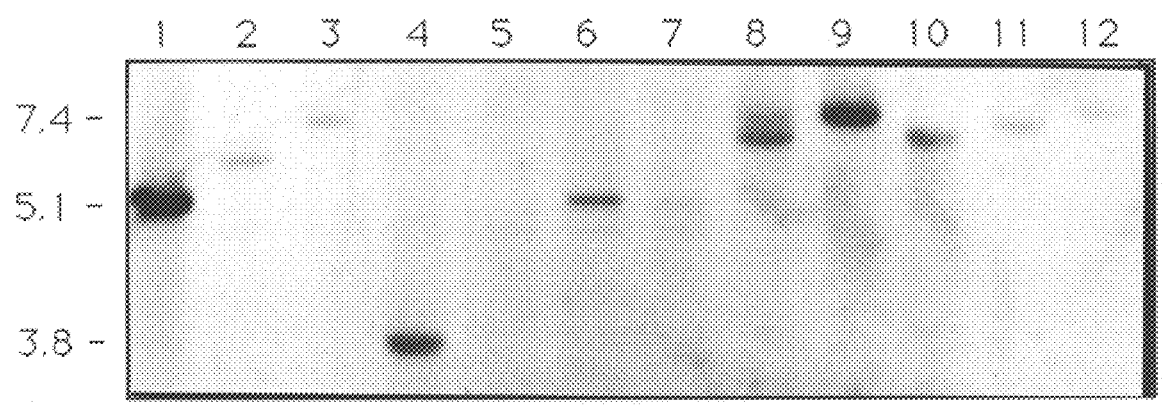
FIG. 7 shows length variation of EcoRI fragments from normal and fragile X human chromosomes with probe pE5.1.

The results of Southern hybridization of EcoR I digested DNA from two normal and seven unrelated fragile X individuals using pE5.1 as probe are shown in FIG. 7. In FIG. 7, Lanes 1, 6 and 7 demonstrate hybridization of the normal 5.1 kb EcoR I fragment in placental DNA (lane 1) and cloned into a cosmid (22.3) or YAC vector (209G4) and seeded into hamster DNA at single-copy level. Somatic cell hybrids containing portions of fragile X chromosomes in hamster backgrounds show bands of altered size from the normal 5.1 kb fragment. Lane 2 contains the hybrid X3000-11.1. Lane 3 contains DNA from micro28D, a proximal hybrid with a breakpoint distal to the fragile site and lane 4 contains DNA from miceo21D, a proximal hybrid with the same chromosome as micro28D, however with a breakpoint detected by pE5.1. Lane 5 contains hamster DNA. Lanes 8–12 contain DNA from 5 unrelated fragile X patients' lymphoblastoid lines. The bands altered from the normal 5.1 kb are seen in each fragile X sample.

The normal samples (two of five normal samples are shown) exhibit the expected 5.1 kb fragment while all seven fragile X patient DNAs exhibited larger EcoR I fragments with variable increases in size, including the 7.4 kb fragment observed from hybrid Y75-1B-M1. These data suggest an insertion or amplification event within the normal 5.1 kb fragment that is specific for the fragile X chromosome and is coincident with the fragile X-associated breakpoint cluster region and the fragile X-related CpG island.

EXAMPLE 13

Identification and Characterization of FMR-1

Figure 8:
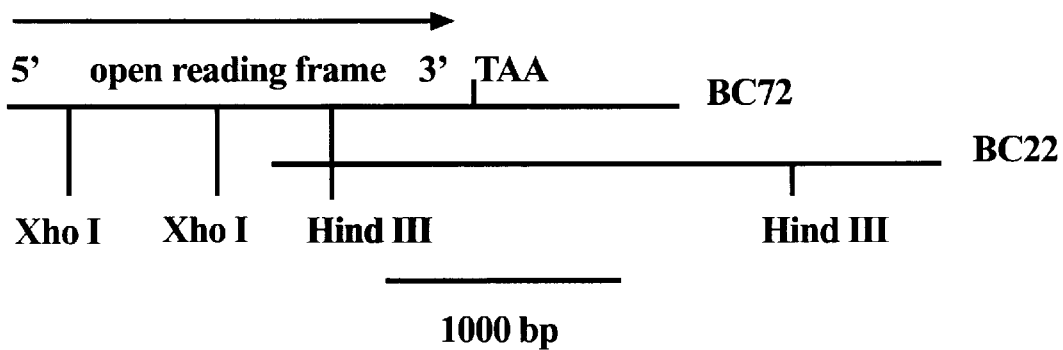
FIG. 8 is a map of the FMR-1 cDNA clones.

In order to search for transcripts associated with the fragile X region, the cosmid subclones of YAC 209G4 were used as hybridization probes to screen a cDNA library derived from normal human fetal brain RNA. Cosmid 4.1, containing BssH II site c (FIG. 4B), identified cDNA clone BC22. A map of FMR-1 cDNA clones is shown in FIG. 8. Restriction digestion and sequence analysis revealed an insert in BC22 of 2835 bp at location 934 to 3765 of SEQ. ID. No. 1, with an open reading frame at one end extending 1033 bp to a stop codon. Since the reading frame remains open at the 5' end of the clone, BC22 was used to identify related cDNAs from the same library. Several overlapping clones were isolated, one of which, BC72, was characterized in greater detail. This clone extended the cDNA sequence another 933 bp in the 5' direction, and overlapped BC22 for approximately 2000 bp toward the 3' end. Sequence analysis demonstrated that the same reading frame remained open through the 5' end of BC72, indicating that the 5' end of the mRNA has not yet been reached, and allowing prediction of a portion (657 amino acids) of the encoded protein. It remains unclear if the entire 3' portion also was isolated since no poly(A) tract was found at the end of BC22, however a putative polyadenylation addition signal is observed in position 3741 following numerous in frame stop codons. In SEQ. ID. No. 1, nucleotides 1–1027 derive from BC72 and nucleotides 934–3765 are from BC22.

A repeated DNA sequence is found close to the 5' end of BC72 with 28 CGG triplets interspersed with two AGG triplets. This CGG repeat encoding 30 contiguous arg residues begins with base 37 and extends to base 127. In the predicted open reading frame, this repeat would generate a protein domain composed of 30 contiguous arginine residues. Homology searches with the predicted protein sequence identify significant overlaps with a number of arginine-rich proteins, although none contain a polyarginine stretch of equivalent length. The remainder of the protein shows no significant homology in protein database searches. However, searches against DNA sequence databases identify several related sequences, the strongest of which is with the human androgen receptor (AR). This is an X-linked gene (mapping to Xq12) with an identical, though smaller, CGG repeat in the first exon which encodes a polyglycine stretch.

EXAMPLE 14

Northern Hybridization

Figure 9:
FIG. 9 is a Northern blot analysis of a poly(A)RNA hybridized with cDNA BC22.

Northern hybridization using the BC22 insert as probe was run. (FIG. 9). Five μg of poly(A) selected RNA from human brain (lane 1) and normal placenta (lane 2) were electrophoresed, blotted onto a GeneScreen Plus filter and hybridized with radiolabeled BC22 insert. A single hybridizing species of approximately 4.8 kb is observed in each lane. As seen in FIG. 9, this procedure detects a mRNA of approximately 4.8 kb in human brain and placenta. This indicates that the 3.8 kb of cDNA obtained does not contain the entire mRNA of this gene. The probe failed to detect signal in human liver, fetal lung and fetal kidney but did detect message in lymphocytes.

EXAMPLE 15

Zoo Blot Analysis

Figure 10:
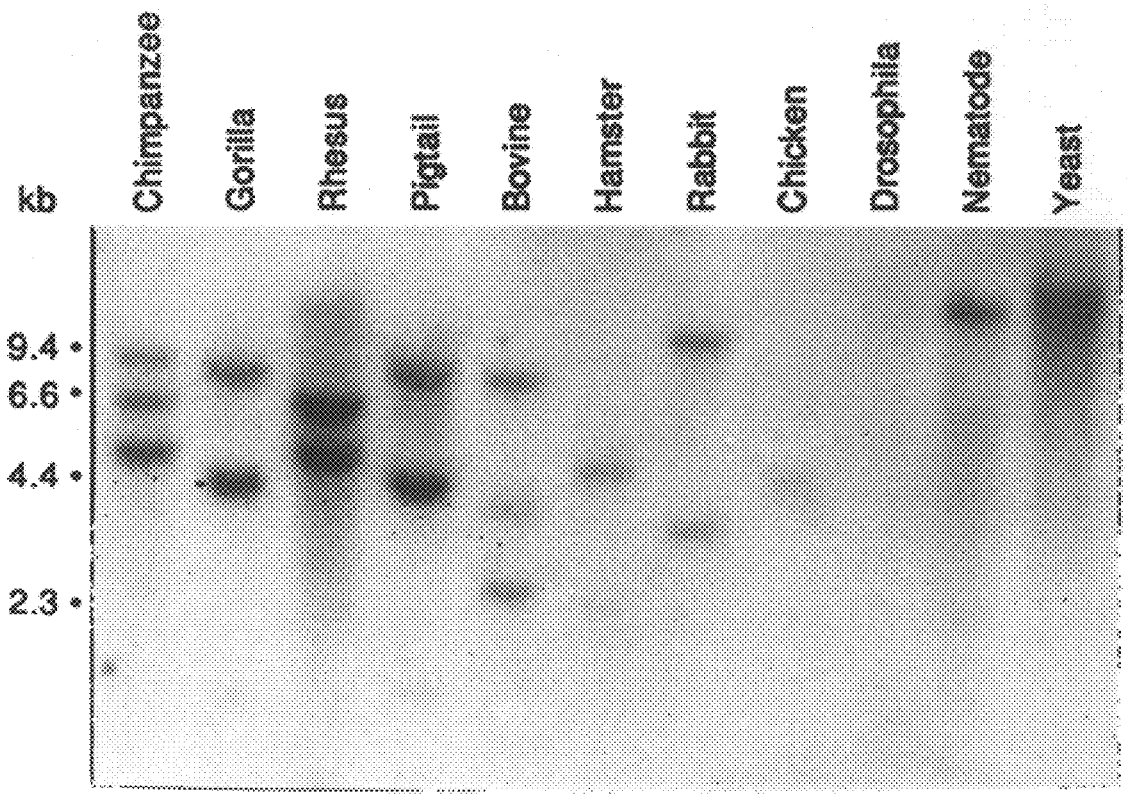
FIG. 10 is a zoo blot analysis of DNA isolated from several species hybridized with cDNA BC22.

Hybridization of BC22 to DNA samples isolated from a number of different organisms was run (FIG. 10). Ten μg of DNA from each species was cleaved with EcoRI and electrophoresed and blotted onto a nylon membrane. Hybridization was carried out with labelled cDNA overnight using standard conditions and washed to a final stringency of 0.2×SSC for 5 min at 65° C. Hybridization signals were observed with all organisms with the exception of *Drosophila melanogaster*. Since this blot was washed under very stringent conditions (final wash in 0.2×SSC at 65° C. for 5 min), cross hybridization may be observed in Drosophila under less stringent conditions. However, the high stringency of the final wash does indicate the highly conserved nature of this sequence particularly in C. elegans.

EXAMPLE 16

Location of FMR-1 Gene Relative to the Fragile X-Related CpG Island and FXBCR

BC22 demonstrates hybridization to the 70 kb fragment of YAC 209G4 between BssH II sites b and c as well as to cosmids 4.1, 34.4, 31.4 and 22.3 (FIG. 4), indicating exons spanning over 80 kb of DNA. The proximal/distal orientation of the transcript was determined by hybridizing end fragments of BC22 to the cosmid contig. Since the 3' end of BC22 detected cosmid 4.1 and the 5' end detected cosmid 22.3, the transcriptional orientation was distal from BssH II site b toward the Xq telomere. This suggests the potential involvement of the fragile X-related CpG island in the regulation of this gene. A 1 kb 5' fragment of BC72 (to the Hind III site at position 1026 of SEQ. ID. No. 1) was used to study the location of the exons encoding this portion of the mRNA in the cosmid and YAC clones. In cosmid 22.3, this probe identifies three EcoR I fragments (FIG. 6A) distal to the BssH II site b. One of the fragments contains the BssH II site (b) as well as the breakpoint cluster region and exhibits length variation in fragile X patients. Restriction mapping and direct sequencing of the 5.1 kb EcoR I fragment using a primer derived from BC72 sequence (position 223 to 246) demonstrated an exon immediately distal to the BssH II site b. This exon contains an Xho I site (position 137 in FMR-1 cDNA sequence) that is found 310 nucleotides from the BssHII II site in genomic DNA (FIG. 6B). This exon also contains the block of CGG repeats which are seen in the sequence analysis of the genomic DNA as well. Thus the CGG repeat block is found within the fragile X-related CpG island and constitutes a portion of this CpG-rich region.

EXAMPLE 17

A PCR Assay to Determine Fragile X Disease

A PCR based test is devised in which the length of genomic DNA at the fragile X site from an individual is determined. In this method the total DNA was extracted from lymphoblastoid cells from fragile X and normal individuals. Oligonucleotide primers (SEQ. ID. No. 10 and SEQ. ID. No. 11) were used in PCR using the following conditions: 94° C. 1 min. 72° 2 min. for 50 cycles and a 7 min final extension at 72° C. The use of 10% dimethylsulfoxide in the reaction is important for enhancing the ability to amplify this GC-rich sequence. The PCR products are visualized after size separation by electrophoresis using ethidium bromide staining. Differences in size between PCR products from normal and fragile X samples are observed, and these correspond to variation in the number of CGG repeats present.

EXAMPLE 18

Elucidation of Fragile X Site

To elucidate the fragile X site at the molecular level, somatic cell hybrids were isolated that contained translocations between rodent chromosomes and the human fragile X chromosome, retaining either human Xpter→q27.3 or human Xq27.3→qter, referred to as proximal or distal translocations, relative to the fragile X site. Since the high frequency and specificity of the chromosome breakage was not observed in normal X hybrids and since the translocation breakpoints map within the same interval defined by polymorphic loci which flank the fragile X locus, these breakpoints are likely to coincide with the fragile X site.

A yeast artificial chromosome (YAC) has been isolated which spans some of these translocation breakpoints and includes polymorphic loci which flank the fragile X locus. Within this region, a fragile X-related CpG island was identified which is aberrantly hypermethylated in patients and most carriers of the fragile X syndrome. Although the significance of this CpG-island hypermethylation remains unclear, these data do imply the presence of a gene, perhaps inactivated by methylation, within a genomic region which includes the fragile X-associated hybrid breakpoints.

All patents and publications mentioned in this specification are indicative of the levels of those skilled in the art to which the invention pertains. All patents and publications are herein incorporated by reference to the same extent as if each individual patent or publication was specifically and individually indicated to be incorporated by reference.

One skilled in the art will readily appreciate that the present invention is well adapted to carry out the objects and attain the ends and advantages mentioned as well those inherent therein. The sequences, methods, procedures and techniques described herein are presently representative of the preferred embodiments and are intended to be exemplary and not intended as limitations on the scope. Changes therein and other uses which are encompassed within the spirit of the invention or defined by the scope of the appended claims will occur to those skilled in the art.

What is claimed is:

1. A method of detecting Fragile X syndrome comprising the step of measuring the expression of the FMR-1 gene, wherein the expression is measured by determining the amount of mRNA expressed, the method comprising the steps of:

extracting RNA from lymphoblastoid cell lines from individuals to be tested;

preparing FMR-1 cDNA and control gene cDNA from said extracted RNA;

quantifying the FMR-1 cDNA by comparing with the control gene cDNA; and comparing the amount of FMR-1 cDNA with the amount of FMR-1 cDNA in normal individuals.

2. The method of claim 1, wherein the quantification step includes PCR of the control gene, electrophoresis of the PCR products, ethidium bromide staining of the products and quantification of FMR-1 products versus control gene products.

3. The method of claim 2, wherein the oligonucleotide primers SEQ. ID. No. 8 and SEQ. ID. No. 9 are used to amplify the mRNA from the fragile X site.

4. The method of claim 3, wherein the control gene is HPRT and the oligonucleotide primers are SEQ. ID. No. 12 and SEQ. ID. No. 13.

* * * * *